United States Patent [19]

Becker

[11] Patent Number: 5,695,494

[45] Date of Patent: Dec. 9, 1997

[54] REM OUTPUT STAGE TOPOLOGY

[75] Inventor: Daniel J. Becker, Broomfield, Colo.

[73] Assignee: Valleylab Inc, Boulder, Colo.

[21] Appl. No.: 362,091

[22] Filed: Dec. 22, 1994

[51] Int. Cl.[6] .................................................. A61B 17/36
[52] U.S. Cl. ...................................... 606/33; 606/32
[58] Field of Search ............................... 606/32–52

[56]  References Cited

U.S. PATENT DOCUMENTS

| | | |
|---|---|---|
| 3,933,157 | 1/1976 | Bjurwill et al. . |
| 4,200,104 | 4/1980 | Harris . |
| 4,384,582 | 5/1983 | Watt ........................... 606/35 |
| 4,416,277 | 11/1983 | Newton et al. . |
| 4,566,454 | 1/1986 | Mehl et al. ................... 606/36 |
| 4,848,355 | 7/1989 | Manes . |
| 5,372,596 | 12/1994 | Klicek et al. ................ 606/34 |

FOREIGN PATENT DOCUMENTS

| | | | |
|---|---|---|---|
| 3604823 | 8/1987 | Germany | ............... 606/34 |
| 0390937 | 4/1989 | Germany | . |

*Primary Examiner*—David M. Shay
*Attorney, Agent, or Firm*—Peter C. Richardson; Lawrence C. Akers; Aaron Passman

[57] ABSTRACT

Apparatus monitors RF return current to maximize the AC signal of impedance at two return electrodes. A transformer with driving and driven windings isolates ESU and patient. At ends of the driving winding are signal and ground terminals joined to the return electrodes with capacitors returning current. An AC coupling capacitor at the signal terminal has a timing circuit in sync to the voltage wave and relative to impedance of the return electrodes. Microprocessing the voltage at the signal terminal of the driving winding watches impedance and determines if the RF return current path is adequate. Voltage detection within the timing circuit has a voltage shaping circuit. A voltage comparator after the voltage detection forms a square wave. A current detection circuit and a coupling capacitor allow AC flow to the driving winding. Current shaping circuit in the current detection circuit has a voltage comparator at the output to form a square wave. Phase detection at the voltage and current detection circuits outputs filters the phase difference that is sampled and held as DC input to a switch, with an output and a few inputs to DC voltages. Phase locking an oscillating voltage source directly and/or through the sample and hold or DC switch tunes oscillation frequency and maximizes the voltage detection circuit output. Monitoring the return current with a signal from the voltage detection circuit connected to an oscillating voltage that is phase locked to the current phase therein shows that no phase difference and maximum signal voltage occur simultaneously.

35 Claims, 3 Drawing Sheets

REM OUTPUT STAGE TOPOLOGY

1. Field of the Invention

This invention pertains to an apparatus and a method of monitoring the return current path in an electrosurgical system, and more particularly, to the use of a phase locked loop in the electrosurgical return path monitoring circuit.

2. Background of the Disclosure

Electrosurgery is the application of high frequency electrical energy to a surgical site on a patient for the purpose of effecting changes to the tissue, typically cutting, coagulating or a combination. High frequency current can be delivered in bipolar fashion, where the current flows between two electrodes through a relatively small quantity of tissue. The second form, pertinent to this invention, is monopolar electrosurgery. In monopolar electrosurgery the high frequency current is delivered by an active electrode that is small enough to cause high current density at the surgical site and thereby effect the tissue. The current returns to the electrosurgical system through the electrosurgical return path to complete the high frequency electrical circuit. The return current path must be of adequate size and of low enough electrical resistance so that no significant heat is produced. If the contact between the patient tissue and the return path is inadequate and causes electrical resistance, tissue burning may occur at a site other than the surgical site. This may be at the return electrode attachment or at some other location on the patients body if electrosurgical current is forced to return to the electrosurgical system through an alternate path.

A particular danger exists at the return electrode attachment to the patient. If, for example, the patient return electrode is misapplied, is partially covering high impedance tissue such as hair or a bony protrusion, or the return electrode conductive gel has partially dried, the return current density may be high enough to cause a burn at the return electrode site. The approach of using a split pad patient return electrode in combination with a contact measuring circuit is well known (see U.S. Pat. No. 3,933,157).

U.S. Pat. No. 4,200,104 describes the circuitry for capacitance measurement between the split pads in order to monitor the area of contact in a split pad patient return electrode where the return electrode is capacitively coupled to the patient. It also discloses a power supply for the monitoring system that prevents neuromuscular stimulation and maintains patient isolation from ground. However the system disclosed is susceptible to high frequency electrosurgical current interference during activation and does not provide circuitry for automatically adapting to different return path and patient impedances.

U.S. Pat. No. 4,416,277 discloses a means for producing a signal which is a function of the impedance between the split pads based on using a separate AC monitoring current that is at a frequency distinct from that of the electrosurgical AC current. The disclosed system is operational and accurate during activation of the electrosurgical current. A monitoring system is disclosed that establishes an upper limit for the impedance, determines if the impedance is within the desired range and changes the monitoring algorithm depending on the type of return electrode.

U.S. Pat. No. 4,848,335 also discloses a system for monitoring the resistance of the return path of either a split pad or single pad return electrode based on using a separate AC monitoring current. A microprocessor is used for monitoring while the upper limit is set manually by the user of the electrosurgical system. Further disclosed is a device for displaying the resistance of the return pad to the user.

U.S. Pat. Nos. 4,416,277 and 4,848,335 both have the disadvantage that there is no automatic adjustment of the AC monitoring current frequency. The disclosed oscillators require manual setting or tuning of the output frequency in order to achieve the best (maximum) signal level of the signal which is a function of the impedance between the split pads. It is an object of the present invention to disclose an apparatus that automatically adjusts the AC monitoring current frequency to match the electrical characteristics of the return path and isolation transformer to achieve an improved signal level using a phase locked loop within the electrosurgical return path circuit. A further object of this invention is disclose a method for using a phase locked loop within an electrosurgical return path circuit.

SUMMARY OF THE INVENTION

An apparatus for monitoring an electrosurgical return current path in a system that automatically maximizes the alternating voltage signal that is proportional to the impedance between the two electrical contacts of a dual patient return electrode. The dual patient return electrode may be carried on a common substrate which is an electrical insulator that can include a pressure sensitive and electrically conductive gel.

The return electrode circuit may have an isolation transformer for isolating the electrosurgical unit from the patient. The isolation transformer can have a driving winding and a driven winding. The driving winding may include a signal terminal and a ground terminal each connected to opposite ends. The driven winding may connect to the dual patient return electrode through two electrical conductors. There may also be two capacitors joined together and attached to the electrical conductors for returning the electrosurgical current to the system on the driven winding side of the isolation transformer.

An alternating voltage coupling capacitor may connect the signal terminal of the driving winding to a timing circuit. The timing circuit would preferably be synchronous with the voltage waveform at the signal terminal. The voltage at the signal terminal is proportional to the impedance between the two electrical contacts of a dual patient return electrode. A microprocessor can preferably be connected to the signal terminal of the driving winding for monitoring the electrical signal proportional to the impedance between the contacts to determine if the electrosurgical current path is adequate;

A voltage detection circuit may be connected to the alternating voltage coupling capacitor. The voltage detection circuit may include a voltage shaping circuit. Following the voltage detection circuit a voltage comparator may be used to produce a waveform that is substantially square in shape. A current detection circuit is preferably in electrical communication with the driving winding. There may be an alternating current coupling capacitor so that only alternating currents are passed. A current shaping circuit may be included in the current detection circuit. Another voltage comparator can be connected to the output of the current detection circuit to produce a waveform that is substantially square in shape.

A phase detector is connected to the outputs of the voltage detection circuit and the current detection circuit. The phase detector may be a logic flip flop. The output of the phase detector corresponds to whether the voltage signal leads or lags the current signal. A phase filter is connected to the output phase detector for providing an appropriate response characteristic of the phase difference signal. A sample and hold circuit may follow the phase filter so that only substantially DC voltages are passed and not radio frequency voltages.

There can be a DC switch, with a single output and a plurality of input positions. One input of the DC switch can electrically communicate with the phase filter and the other input positions can each be connected to specific DC voltages. The DC switch can preferably be used to allow selection of either the filtered phase difference signal or one of the specific DC voltages. A phase locked oscillating voltage source communicates with the phase filter either directly, or alternately, through either the sample and hold circuit or DC switch, or both. The phase locked oscillating voltage source will continuously adjust the frequency of oscillation so as minimize the phase difference between the voltage and current waveforms on the signal terminal of the driving winding. This most preferably causes the phase locked oscillating voltage source to automatically maximize the alternating voltage signal that is proportional to the impedance between the two electrical contacts of a dual patient return electrode.

The phase locked oscillating voltage source may include a voltage controlled oscillator. A duty cycle correcting device may be connected to the output of the phase locked oscillating voltage source for producing a duty cycle of substantially one half the waveform period. There can be an AC switch, with a single output and a plurality of input positions. One input can be in electrical communication with the phase locked oscillating voltage source and the other inputs can each be connected to a fixed frequency oscillating voltage source. Either the phase locked oscillating voltage source signal or a plurality of fixed frequency oscillating voltages may be selected. There can be a resistor in series with a capacitor connecting the signal terminal of the driving winding and in electrical communication with the phase locked oscillating voltage source, the series combination providing a voltage representation of current and preventing DC current flow in the driving winding.

A method of using an electrosurgical return electrode circuit for monitoring electrosurgical current including the step of producing an electrical signal proportional to the impedance between two electrical contacts of a dual patient return electrode. The method may have the step of applying two patient contact pads, which are carried on an electrically insulating common substrate, to a patient. Alternatively, there can be the step of attaching the two patient contact pads, on a common substrate with a pressure sensitive and electrically conductive gel, to a patient.

There is the step of producing an electrical signal proportional to the impedance between the first and the second contact pads at the signal terminal of the driving winding. The step of detecting the electrical signal proportional to the impedance between the first and second contact pads with a voltage detection circuit follows. The step of shaping the voltage in the voltage detection circuit with a voltage shaping circuit may follow. There can be the step of monitoring the electrical signal proportional to the impedance between the first and the second contact pads. There is the step of producing an electrical phase signal of the current flowing in the driving winding by connecting a current detection circuit to the signal terminal of the driving winding. Then the step of shaping the electrical phase signal of the current with a current shaping circuit might be used. The method may also include the steps of coupling only alternating voltage signals to the voltage detection circuit and only alternating current signals to the current detection circuit with capacitors connecting the driving winding with the voltage and current detection circuits. Next there is the step of providing an electrical signal indicating the phase difference between the voltage and current using a phase detector connected to the voltage shaping circuit and the current shaping circuit. The step of providing the phase difference signal with a logic flip flop device to communicate with both the voltage shaping circuit and the current shaping circuit may be employed. Thereafter is the step of providing an appropriate response characteristic of the phase difference signal with a phase filter. Next is the step of producing an electrical driving signal upon receipt of the appropriate response of the phase difference signal, the electrical driving signal having a frequency of oscillation that is continuously adjusted to keep the phase difference between the voltage and the current at the signal terminal substantially zero while producing a maximum voltage signal at the signal terminal of the driving winding with a phase locked oscillating voltage source connected between the phase filter and the signal terminal of the driving winding. Providing a voltage representation of current and preventing DC current flow in the driving winding with a resistor connected in series to a capacitor between the driving winding and the phase locked oscillating voltage source may be another step. An additional step may be signalling the driving winding with a voltage controlled oscillation according to the phase difference signal between the current and voltage waveforms at the driving winding. Alternatively this step could be oscillating a voltage signal to the driving winding with an adjustable timer to connect between the phase difference signal and the driving winding.

There may be the step of receiving an appropriate response characteristic of the phase difference signal with a sample and hold circuit connected between the phase filter and the phase locked oscillating voltage source, the sample and hold circuit passing substantially DC voltages and not passing radio frequency voltages to the phase locked oscillating voltage source. There may be an additional step of selecting specific portions of the waveform of the electrical signal proportional to the impedance between the two patient contact pads with a voltage detection circuit which is a timing circuit that is synchronous with the phase locked oscillating voltage source. There may a further step of monitoring whether the electrosurgical current path is adequate with a microprocessor in electrical communication with the signal terminal of the driving winding to measure the electrical signal proportional to the impedance between the first and the second patient contact pads.

The method can have the step of selecting either the phase locked oscillating voltage signal or a plurality of fixed frequency oscillating voltages with a switch with a plurality of inputs, one input connected to the phase locked oscillating voltage source and the other inputs each connected to a fixed frequency oscillating voltage source, the output connected to the driving winding. There may also be the step of providing specific oscillating frequencies with a switch with a plurality of input positions connected between the phase filter and the phase locked oscillating voltage source, the first input connected to the phase filter and the other inputs each connected to a specific voltage, for causing the phase locked oscillating voltage source to provide either the frequency determined by the phase filter output or a specific, and fixed, oscillating frequency.

The method may include the step of correcting the phase locked oscillating voltage source waveform to a duty cycle of substantially one half the waveform period with a duty cycle correcting circuit connected between the phase locked oscillating voltage source and the signal terminal of the driving winding. There can be the steps of forming waveforms that are generally square in shape with voltage comparators whose inputs connect to the voltage detection circuit and current detection circuit with the outputs connecting to the phase detector.

DESCRIPTION OF THE PREFERRED EMBODIMENT

Figure 1:
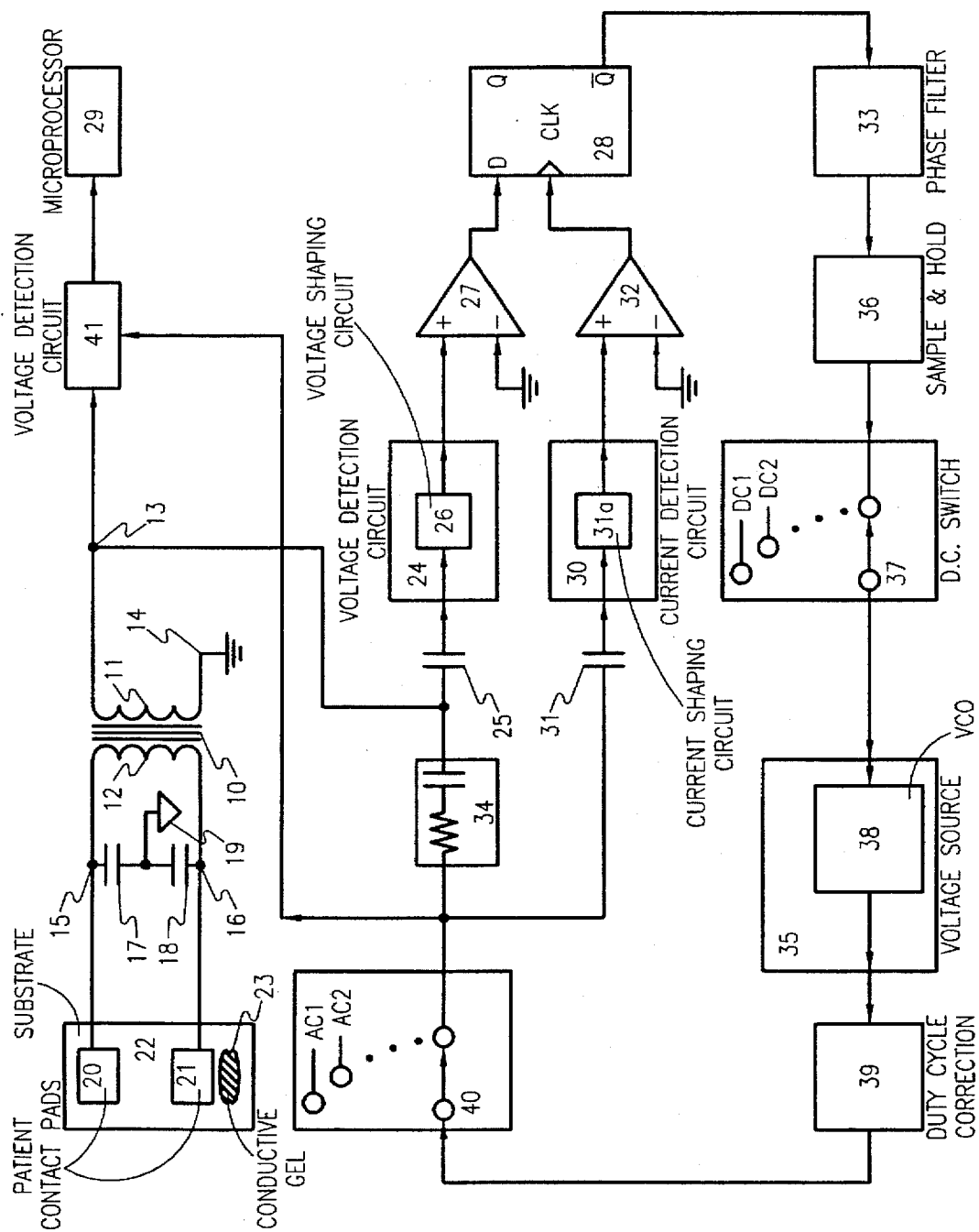
FIG. 1 is a combined schematic and block diagram of illustrative circuitry for the apparatus for monitoring an electrosurgical return path of the present invention.

Referring now to FIG. 1, a combined schematic and block diagram of a system for monitoring electrosurgical current is shown. The circuit includes an isolation transformer 10 in the electrosurgical return electrode circuit. In the preferred embodiment, the isolation transformer 10 is a square core and fixed gap custom made by Magnelab Corporation in Boulder, Colo., that provides a high Q at a driving frequency near 80 Khz. The isolation transformer 10 has two windings, a driving winding 11 and a driven winding 12. The driving winding 11 has a signal terminal 13 and a ground terminal 14 at opposing ends thereof. Two capacitors 17 and 18 are connected in series between the electrical conductors 15 and 16 near the driven winding 12. An electrosurgical return current connection 19 is formed by electrical coupling through each of these capacitors 17 and 18 to a circuit node at their juncture.

Two patient contact pads 20 and 21 are electrically connected to the electrical conductors 15 and 16 at the ends opposite the driven winding 12. In the preferred embodiment, the two patient contact pads 20 and 21 are carried on an electrically insulating common substrate 22. Most preferably, this common substrate includes a pressure sensitive and electrically conductive gel 23 e.g. Polyhesive® of Valleylab Incorporated, Boulder, Colo. Valleylab REM pads E7507 and E7510 include the electrical conductors 15 and 16, the two patient contact pads 20 and 21 in FIG. 1, the electrically insulating common substrate 22, and a pressure sensitive and electrically conductive gel 23. They have been shown to perform well in a variety of surgical applications, and when tested with the preferred embodiment of the present invention.

A voltage detection circuit 24 is connected to the signal terminal 13 of the driving winding 11 shown in FIG. 1. Most preferably, an alternating voltage coupling capacitor 25 is connected between the driving winding 11 and the voltage detection circuit 24 so that only alternating voltage signals are communicated thereacross. The voltage detection circuit 24 produces an electrical signal proportional to the phase of the voltage driving signal.

A voltage shaping circuit 26 is included in the voltage detection circuit 24. The voltage detection circuit 24 may preferably be followed by a voltage comparator 27 with one input connecting to the voltage detection circuit 24 and the other to a fixed voltage or signal ground so that the output waveform is generally square in shape. The output of the voltage detection circuit 24 or alternately the voltage comparator 27 is connected to a phase detector 28. In the preferred embodiment, the phase detector 28 is a logic flip flop device such as the CD4013 made by National Semiconductor Corporation, Santa Clara, Calif. Most preferably, a microprocessor device 29 is in electrical communication with the signal terminal 13 for monitoring the signal proportional to the impedance between the two patient contact pads 20 and 21 for determining if the electrosurgical current path is adequate. In the preferred embodiment, the 80C562 microprocessor, manufactured by Phillips Semiconductors, Eindhoven, the Netherlands, with built in analog to digital channels, is used for monitoring.

A current detection circuit 30 is also connected to the signal terminal 13 of the driving winding 11 in parallel to the voltage detection circuit 24. A capacitor 31 is connected between the signal terminal 13 of the driving winding 11 and the current detection circuit 30 so that only alternating current signals are communicated thereacross. In the preferred embodiment, a resistor in series with a capacitor 34 is connected between the signal terminal 13 of the driving winding 11 and the current detection circuit 30 for providing a voltage representation of current and preventing DC current flow in the driving winding 11.

The current detection circuit 30 produces an electrical phase signal of the current flowing in the driving winding 11. A current shaping circuit 31a is included in the current detection circuit 30. The current detection circuit 30 may preferably be followed by a voltage comparator 32 with one input connecting to the current detection circuit 30 and the other to a fixed voltage or signal ground so that the output is generally square in shape. The output of the current detection circuit 30 or alternately the voltage comparator 32 is also connected to the phase detector 28 so that the phase detector 28 electrically communicates with both the voltage detection circuit 24 and the current detection circuit 30. The phase detector 28 provides an electrical signal indicating the phase difference between the voltage and current waveforms at the signal terminal 13 of the driving winding 11.

A phase filter 33 is connected to the output of the phase detector 28 for providing an appropriate response characteristic of the phase difference signal such that the closed loop system is stable. A phase locked oscillating voltage source 35 is connected between the output of the phase filter 33 and the signal terminal 13 of the driving winding 11. The output of the phase locked oscillating voltage source 35 completes a feedback loop back to the signal terminal 13 of the driving winding 11. This oscillating voltage source produces an electrical driving signal derived from the filtered phase difference signal. The frequency of oscillation is continuously adjusted to keep the phase difference between the voltage and the current at the signal terminal 13 substantially zero.

In the preferred embodiment, a sample and hold circuit 36 is connected to the phase filter 33 for maintaining the appropriate response characteristic of the phase difference signal. The sample and hold circuit 36 passes only substantially DC voltages or low frequency voltages and does not pass radio frequencies. A DG445 integrated circuit manufactured by Silicon Incorporated, Santa Clara, Calif. has been found to perform well for the sampling function.

A DC switch 37 with multiple input positions would also be in electrical communication with the phase filter 33. One input would receive the filtered phase difference signal and other input positions would each be connected to specific DC voltages, DC1, DC2, and so on. The DC switch would allow selection of either the filtered phase difference signal or one of the specific DC voltages, DC1, DC2, and so on, to provide a way to force the phase locked oscillating voltage source 35 to specific oscillating frequencies in the case of case of circuit start up, error conditions or for testing purposes.

In the preferred embodiment, the phase locked oscillating voltage source 35 includes a voltage controlled oscillator 38. The voltage controlled oscillator 38 responds to the voltage representation of the filtered phase difference signal with proportional changes of frequency. In one embodiment, an adjustable timer is used as the voltage controlled oscillator 38. The NE555N timer manufactured by National Semiconductor, Santa Clara, Calif., has been found to perform adequately as a voltage controlled oscillator.

The preferred embodiment also includes a duty cycle correcting device 39 with its input connected to the output of the phase locked oscillating voltage source 35 so that the driving voltage to the driving winding 11 has a duty cycle that is approximately one half the period of the phase locked oscillating voltage source 35.

It is also preferable to place an AC switch 40 for passing alternating electrical signals in electrical communication with the phase locked oscillating voltage source 35 and the driven winding 12. One switch input connects to the output of the phase locked oscillating voltage source 35 or alternately with the duty cycle correcting device 39. The other inputs AC1, AC2, and so on, are each connected to fixed frequency oscillating voltage sources. Therefore, the AC switch 40 may be positioned to override the signal originating from the phase locked oscillating voltage source 35 in the case of circuit start up, error conditions or for testing purposes.

Figure 2:
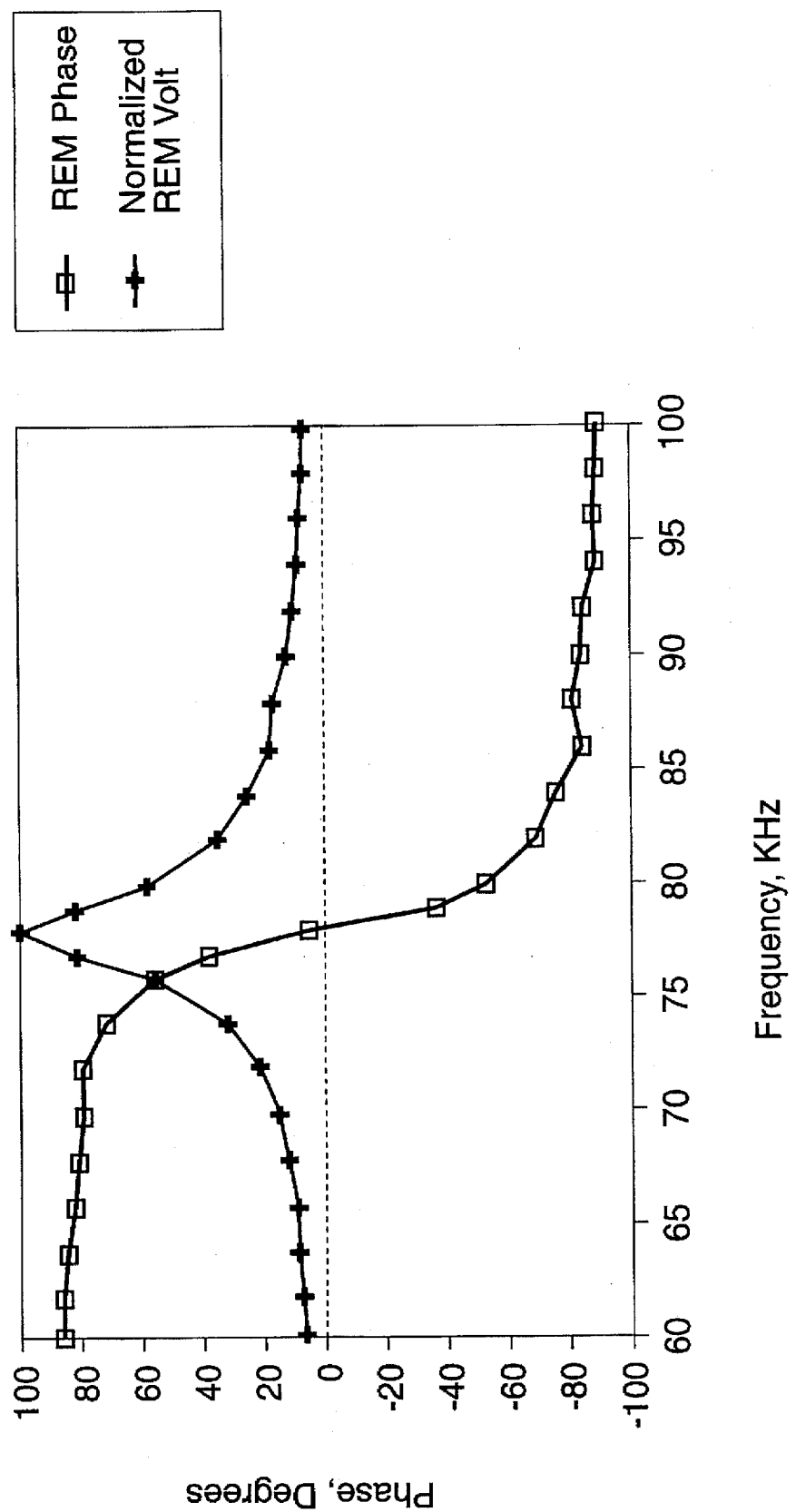
FIG. 2 is a graph showing the relationship of the output voltage of the voltage detection circuit and the phase of the current waveform to the voltage waveform in the driven winding of the isolation transformer.

Referring now to FIG. 2, there is shown a graph of the phase difference between current and voltage in the driving winding 11 and its relationship to the normalized voltage in the driving winding 11. In particular for the present invention, note that the voltage in the driving winding 11 of the isolation transformer 10 reaches a distinct peak. This peak occurs when the phase difference between current and voltage in the driving winding 11 is substantially zero. The phase locked loop of FIG. 1 as described herein operates to keep the phase difference between current and voltage substantially zero and therefore maximizes the voltage signal that is proportional to impedance between the two patient contact pads.

Figure 3:
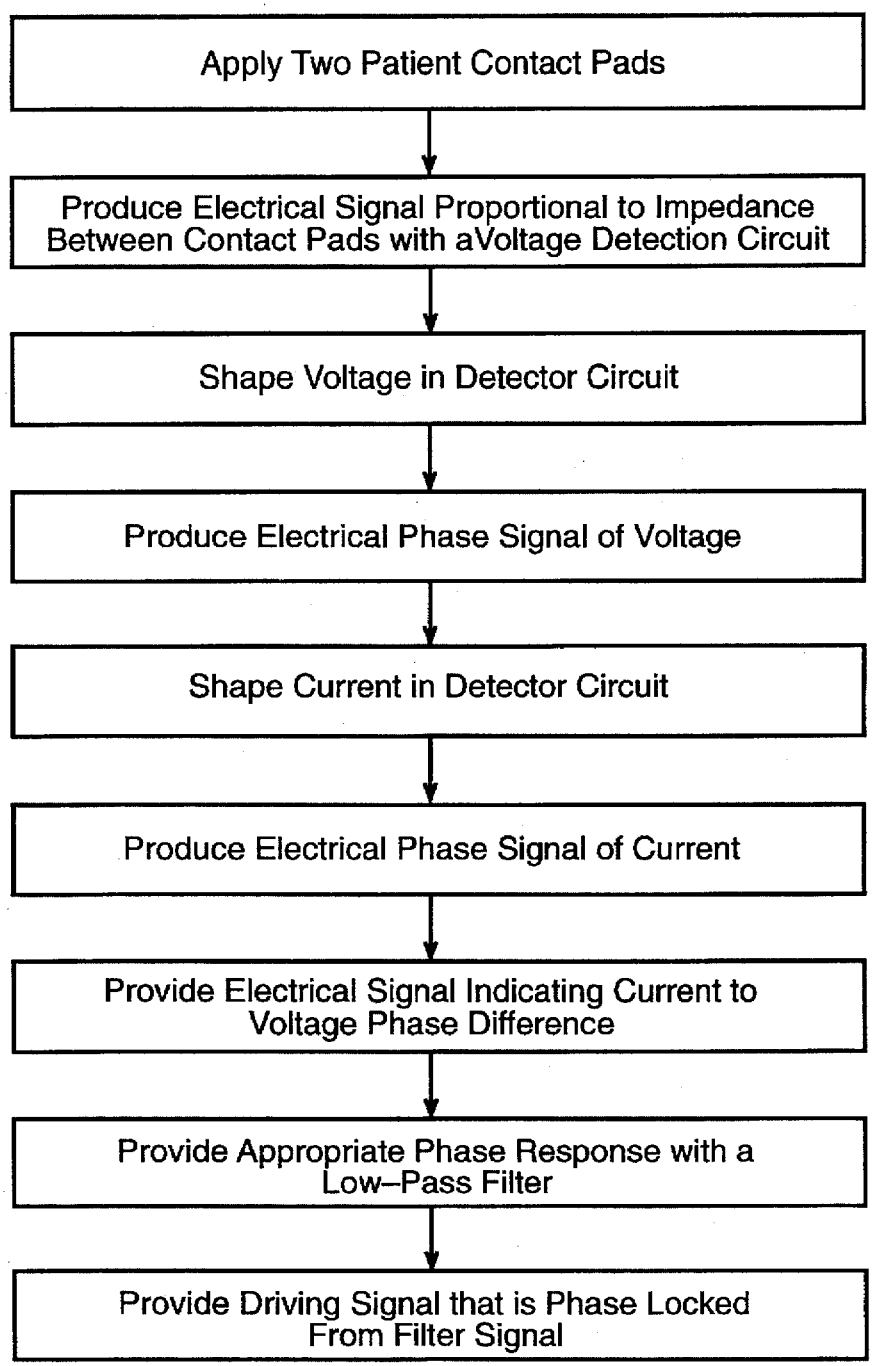
FIG. 3 is a flow chart showing the preferred sequence of steps for using the present invention to monitor electrosurgical current.

Referring now to FIG. 3, the steps for using the system for monitoring electrosurgical return at the return current connection are shown. Attaching the two patient contact pads 20 and 21 to the patient is the first part of the method. The two patient contact pads 20 and 21 may be carried on an electrically insulating common substrate 22 or they may be on a common electrically insulating substrate 22 with a pressure sensitive and electrically conductive gel. The step of producing an electrical signal proportional to the impedance between the two patient contact pads 20 and 21 with a voltage detection circuit connected to the signal terminal 13 of the driving winding 11 follows. It is preferred that the voltage detection circuit 41 be a timing circuit that is synchronous with the phase locked oscillating voltage source 35. The preferred but optional step of shaping the voltage in the voltage detection circuit 24 with a voltage shaping circuit 26 is shown next. An optional and not shown step is monitoring the electrical signal proportional to the impedance between the two patient contact pads 20 and 21 with a microprocessor 29 in electrical communication with the signal terminal 13 of the driving winding 11.

There is the step of producing an electrical phase signal of the current flowing in the driving winding 11 by connecting a current detection circuit 30 to the signal terminal 13 of the driving winding 11. Then the optional and preferred step of shaping the electrical phase signal of the current with a current shaping circuit 31a is shown. The steps of coupling only alternating voltage signals to the voltage detection circuit 24 and only alternating current signals to the current detection circuit 30 with capacitors 25 and 31 connecting the driving winding 11 with the voltage and current detection circuits 24 and 30 are optional and are omitted from FIG. 3 for clarity.

Next there is shown on FIG. 3 the step of providing an electrical signal indicating the phase difference between the voltage and current using a phase detector 28 connected to the voltage shaping circuit 26 and the current shaping circuit 31a. Providing the phase difference signal with a logic flip flop device is preferred. Alternately, the phase relationships could be determined directly with microprocessor 29 or an independent microprocessor or Programed Array Logic. The step of providing an appropriate response characteristic of the phase difference signal with a phase filter 33 is shown next. The step of producing an electrical driving signal from the filtered phase difference signal follows.

Not shown on FIG. 3 is the preferred step of providing a voltage representation of current and preventing DC current flow in the driving winding 11 with a resistor connected in series to a capacitor 34 between the driving winding 11 and the phase locked oscillating voltage source 35. Another method of sensing current could be used such as an optical isolator or current transformer or differentially measuring the voltage across the resistor that is in series with the capacitor. An additional preferred step omitted from FIG. 3 for clarity may be signalling the driving winding 11 with a voltage controlled oscillation according to the phase difference signal between the current and voltage waveforms at the driving winding 11. Alternatively, this step could be oscillating a voltage signal to the driving winding 11 with an adjustable timer to connect between the phase difference signal and the driving winding 11.

Not shown on FIG. 3 is the preferred step of receiving an appropriate response characteristic of the phase difference signal with a sample and hold circuit 36 connected between the phase filter 33 and the phase locked oscillating voltage source 35. It is preferred that the method also have the step of selecting either the phase locked oscillating voltage signal or a plurality of fixed frequency oscillating voltages with an AC switch 40 but the step is omitted from FIG. 3 for clarity. There may also be an optional step of providing specific oscillating frequencies with a DC switch with a plurality of input positions connected between the phase filter 33 and the phase locked oscillating voltage source 35 for causing the phase locked oscillating voltage source 35 to provide either the frequency determined by the phase filter 33 output or a specific, and fixed, oscillating frequency.

The optional step of correcting the phase locked oscillating voltage source waveform to a duty cycle of substantially one half the waveform period with a duty cycle correcting circuit 39 connected between the phase locked oscillating voltage source 35 and the signal terminal 13 of the driving winding 11 is omitted from FIG. 3 for clarity.

In the preferred embodiment, the voltage detection circuit 24 is a timing circuit that is synchronous with the voltage signal applied to the driving winding 11.

What is claimed is:

1. An electrosurgical return electrode circuit for developing an impedance measurement between two contact pads, comprising:

an isolation transformer in the electrosurgical return electrode circuit, the isolation transformer having a driving winding and a driven winding having two driven ends and, the driving winding having two driving ends and having a signal terminal and a ground terminal each connected to one driving end thereof;

a first electrical conductor and a second electrical conductor each attached to one driven end of the driven winding;

a first patient contact pad and a second patient contact pad electrically coupled to the first and second electrical conductors, respectively, and the driven winding for resonating at a monitoring frequency;

a voltage detection circuit connected to the signal terminal of the driving winding for producing an electrical phase signal of the voltage across the driven winding;

a voltage shaping circuit included in the voltage detection circuit and in electrical communication therewith;

a current detection circuit connected to the signal terminal of the driving winding for producing an electrical phase signal of the current flowing in the driving winding;

a current shaping circuit included in the current detection circuit and in electrical communication therewith;

a phase detector connected to the voltage shaping circuit and the current shaping circuit for providing an electrical signal indicating a phase difference signal between the voltage across the signal terminal and current at the signal terminal;

a phase filter connected to the phase detector for providing a response characteristic of the phase difference signal, and a phase locked oscillating voltage source for operating at the monitoring frequency of oscillation, the phase locked oscillating voltage source connected between the phase filter and the signal terminal of the driving winding for producing an electrical driving signal upon receipt of the response characteristic of the phase difference signal so that the monitoring frequency of oscillation is continuously adjusted to keep the phase difference between the voltage and the current at the signal terminal substantially zero thereby delivering a maximum voltage signal to the voltage detection circuit, the electrical driving signal used to develop the impedance measurement.

2. The electrosurgical return electrode circuit of claim 1, wherein the first and the second patient contact pads are carried on a common substrate which is an electrical insulator.

3. The electrosurgical return electrode circuit of claim 1, wherein the first and the second patient contact pads are carried on a common substrate with an electrically conductive gel.

4. The electrosurgical return electrode circuit of claim 1, wherein a sample and hold circuit is connected between the phase filter and the phase locked oscillating voltage source for receiving the response characteristic of the phase difference signal, the sample and hold circuit passing substantially DC voltages and not passing radio frequency voltages to the phase locked oscillating voltage source.

5. The electrosurgical return electrode circuit of claim 1, wherein the voltage detection circuit is a timing circuit synchronous with the phase locked oscillating voltage source for selecting specific portions of the monitoring waveform of the electrical signal proportional to the impedance between the first and second patient contact pads.

6. The electrosurgical return electrode circuit of claim 1, wherein a microprocessor is in electrical communication with the signal terminal of the driving winding for monitoring the monitoring waveform of the electrical signal proportional to the impedance between the first and second patient contact pads to determine if the electrosurgical current path is adequate.

7. The electrosurgical return electrode circuit of claim 1, wherein a switch with a plurality of inputs, one input is connected to the phase locked oscillating voltage source and the other inputs are each connected to a fixed frequency oscillating voltage source, an output connected to the driving winding so that either the phase locked oscillating voltage source signal or a plurality of fixed frequency oscillating voltages may be selected.

8. The electrosurgical return electrode circuit of claim 1, wherein a duty cycle correcting device is connected between the phase locked oscillating voltage source and the driving winding for correcting the phase locked oscillating voltage source waveform to a duty cycle of substantially one half.

9. The electrosurgical return electrode circuit of claim 1, wherein a switch with a plurality of input positions is connected between the phase filter and the phase locked oscillating voltage source, the first input connected to the phase filter and the other inputs each connected to a specific voltage, for causing the phase locked oscillating voltage source to provide either the frequency determined by the phase filter output or a specific oscillating frequency.

10. The electrosurgical return electrode circuit of claim 1, wherein a logic flip flop device or microprocessor communicates with both the voltage shaping circuit and the current shaping circuit for providing the phase difference signal.

11. The electrosurgical return electrode circuit of claim 10, wherein the microprocessor with a first input, a second input and at least one output the first connected to the single output of the first voltage comparator, the second input connected to the single output of the second voltage comparator so the output of the microprocessor is a phase difference signal.

12. The electrosurgical return electrode circuit of claim 1, wherein a voltage comparator input connects to the voltage detection circuit and the comparator output connects to the phase detector to form a waveform that is generally square in shape.

13. The electrosurgical return electrode circuit of claim 1, wherein a voltage comparator input connects to the current detection circuit and the comparator output is connected to the phase detector to form a waveform that is generally square in shape.

14. The electrosurgical return electrode circuit of claim 1, wherein a capacitor is connected between the driving winding and the voltage detection circuit for coupling only alternating voltage signals therebetween.

15. The electrosurgical return electrode circuit of claim 1, wherein a capacitor is connected between the driving winding and the current detection circuit for coupling only alternating current signals therebetween.

16. The electrosurgical return electrode circuit of claim 1, wherein a resistor is connected in series with a capacitor between the driving winding and the phase locked oscillating voltage source, the series combination providing a voltage representation of current and preventing DC current flow in the driving winding.

17. The electrosurgical return electrode circuit of claim 1, wherein a voltage controlled oscillator is included in the phase locked oscillating voltage source.

18. The electrosurgical return electrode circuit of claim 1, wherein an adjustable timer is included in the phase locked oscillating voltage source.

19. A method of using an electrosurgical return electrode circuit to measure impedance between two contact pads, the circuit having an isolation transformer, the isolation transformer having a driving winding and a driven winding, the driving winding having a signal terminal and a ground terminal each connected to an end thereof, a first electrical conductor and a second electrical conductor attached to the first and second end, respectively, of the driven winding, an electrosurgical return current connection connected to the driven winding to provide a return path for electrosurgical current so the electrosurgical return current connection is in series with each end of the driven winding of the isolation transformer, a first and a second patient contact pad electrically coupled to the first and second electrical conductors, respectively, and the driven winding, the method of using comprising the steps of:

producing an electrical phase signal proportional to the voltage across the driving winding with a voltage detection circuit connected to the signal terminal of the driving winding;

shaping the voltage in the voltage detection circuit with a voltage shaping circuit connected to the voltage detection circuit;

monitoring the electrical signal proportional to the impedance between the first and the second contact pads by connecting a voltage detection circuit across the signal terminal of the driving winding;

producing an electrical phase signal of the current flowing in the driving winding by connecting a current detection circuit to the signal terminal of the driving winding;

shaping the electrical phase signal of the current in the current detection circuit with a current shaping circuit connected to the current detection circuit;

providing an electrical signal indicating the phase relationship between the voltage across the signal terminal and current at the signal terminal with a phase detector connected to the voltage shaping circuit and the current shaping circuit;

providing a response characteristic of the phase difference signal with a phase filter connected to the phase detector for providing the response characteristic of the phase difference signal, and producing an electrical driving signal upon receipt of the response characteristic of the phase difference signal so that a monitoring frequency of oscillation is continuously adjusted to keep the phase difference between the voltage across the signal terminal and the current at the signal terminal substantially zero for delivering a maximum voltage signal to the voltage detection circuit with a phase locked oscillating voltage source connected between the phase filter and the signal terminal of the driving winding;

measuring the impedance between the first and second patient contact pads using the driving signal as a source for developing the measurement.

20. The method of using an electrosurgical return electrode circuit for monitoring electrosurgical current of claim 19, having the step of applying the first and the second patient contact pads, which are carried on an electrically insulating common substrate, to a patient.

21. The method of using an electrosurgical return electrode circuit for monitoring electrosurgical current of claim 19, having the step of attaching the first and the second patient contact pads, on a common substrate with an electrically conductive gel, to a patient.

22. The method of using an electrosurgical return electrode circuit for monitoring electrosurgical current of claim 19, having the step of receiving a response characteristic of the phase difference signal with a sample and hold circuit connected between the phase filter and the phase locked oscillating voltage source, the sample and hold circuit passing substantially DC voltages and not passing radio frequency voltages to the phase locked oscillating voltage source.

23. The method of using an electrosurgical return electrode circuit for monitoring electrosurgical current of claim 19, having the step of selecting specific portions of the electrical signal proportional to the impedance between the first and the second patient contact pads waveform with a voltage detection circuit which is a timing circuit that is synchronous with the phase locked oscillating voltage source.

24. The method of using an electrosurgical return electrode circuit for monitoring electrosurgical current of claim 19, having the step of monitoring whether the electrosurgical current connection is adequate with a microprocessor in electrical communication with the signal terminal of the driving winding to measure the electrical signal proportional to the impedance between the first and the second patient contact pads.

25. The method of using an electrosurgical return electrode circuit for monitoring electrosurgical current of claim 19, having the step of selecting either the phase locked oscillating voltage signal or a plurality of fixed frequency oscillating voltages with a switch with a plurality of inputs, one input connected to the phase locked oscillating voltage source and the other inputs each connected to a fixed frequency oscillating voltage source, the output connected to the driving winding.

26. The method of using an electrosurgical return electrode circuit for monitoring electrosurgical current of claim 19, having the step of correcting the phase locked oscillating voltage source waveform to a duty cycle of substantially one half the waveform period with a duty cycle correcting circuit connected between the phase locked oscillating voltage source and the signal terminal of the driving winding.

27. The method of using an electrosurgical return electrode circuit for monitoring electrosurgical current of claim 19, having the step of providing specific oscillating frequencies with a switch with a plurality of input positions connected between the phase filter and the phase locked oscillating voltage source, the first input connected to the phase filter and the other inputs each connected to a specific voltage, for causing the phase locked oscillating voltage source to provide either the frequency determined by the phase filter output or a specific, and fixed, oscillating frequency.

28. The method of using an electrosurgical return electrode circuit for monitoring electrosurgical current of claim 19, having the step of providing the phase difference signal with a logic flip flop device to communicate with both the voltage shaping circuit and the current shaping circuit.

29. The method of using an electrosurgical return electrode circuit for monitoring electrosurgical current of claim 19, having the step of forming a waveform that is generally square in shape with a voltage comparator whose input connects to the voltage detection circuit and whose output connects to the phase detector.

30. The method of using an electrosurgical return electrode circuit for monitoring electrosurgical current of claim 19, having the step of forming a waveform that is generally square in shape with a voltage comparator whose input connects to the current detection circuit and whose output connects to the phase detector.

31. The method of using an electrosurgical return electrode circuit for monitoring electrosurgical current of claim 19, having the step of coupling only alternating voltage signals to the voltage detection circuit with a capacitor connecting the driving winding and the voltage detection circuit.

32. The method of using an electrosurgical return electrode circuit for monitoring electrosurgical current of claim 19, having the step of coupling only alternating current signals to the current detection circuit with a capacitor connecting the driving winding and the current detection circuit.

33. The method of using an electrosurgical return electrode circuit for monitoring electrosurgical current of claim 19, having the step of providing a voltage representation of current and preventing DC current flow in the driving winding with a resistor connected in series to a capacitor between the driving winding and the phase locked oscillating voltage source.

34. The method of using an electrosurgical return electrode circuit for monitoring electrosurgical current of claim 19, having the step of signalling the driving winding with a voltage controlled oscillation according to the phase difference signal between the current and voltage waveforms at the driving winding.

35. The method of using an electrosurgical return electrode circuit for monitoring electrosurgical current of claim 19, having the step of oscillating a voltage signal to the driving winding with an adjustable timer to connect between the phase difference signal and the driving winding.

* * * * *